US008337841B2

(12) United States Patent
Kojima (10) Patent No.: US 8,337,841 B2
(45) Date of Patent: Dec. 25, 2012

(54) METHODS OF SCREENING FOR ANTIBODY LIGHT CHAINS

(75) Inventor: Tetsuo Kojima, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/542,839

(22) PCT Filed: Jan. 21, 2004

(86) PCT No.: PCT/JP2004/000496
§ 371 (c)(1),
(2), (4) Date: Dec. 13, 2005

(87) PCT Pub. No.: WO2004/065611
PCT Pub. Date: Aug. 5, 2004

(65) Prior Publication Data
US 2006/0159673 A1   Jul. 20, 2006

(30) Foreign Application Priority Data

Jan. 21, 2003   (JP) .................................. 2003-012648

(51) Int. Cl.
*A61K 39/395* (2006.01)
*C12N 1/21* (2006.01)
*C12N 15/74* (2006.01)
*C40B 40/10* (2006.01)

(52) U.S. Cl. ................. 424/133.1; 435/252.33; 435/472; 435/7.1

(58) Field of Classification Search ............... 424/133.1; 435/7.1, 252.33, 472
See application file for complete search history.

(56) References Cited

U.S. PATENT DOCUMENTS

| 2004/0219643 | A1* | 11/2004 | Winter et al. ............... 435/70.21 |
| 2006/0269989 | A1 | 11/2006 | Miyazaki et al. |
| 2007/0087381 | A1 | 4/2007 | Kojima |
| 2008/0167193 | A1* | 7/2008 | Zauderer et al. ................. 506/1 |

FOREIGN PATENT DOCUMENTS

| CA | 2 331 641 | 11/1999 |
| DE | 198 19 846 | 11/1999 |
| EP | 0774511 | 5/1997 |
| JP | 2001-523971 | 11/2001 |
| WO | WO 96/34892 | 11/1996 |
| WO | WO 98/50431 | 11/1998 |
| WO | WO 00/44788 | 8/2000 |
| WO | WO 01/44282 | 6/2001 |
| WO | WO 01/70775 | 9/2001 |
| WO | WO 03/087163 | 10/2003 |
| WO | WO 2004/009618 | * 1/2004 |

OTHER PUBLICATIONS

Goldstein et al. (J. Immunol. 158:872-879 (1997)).*
Kipriyanov et al. (Molec. Biol. 12: pp. 173-201 (1999)).*
Pilkington et al. (Molec. Immunol. 33:439-450 (1996)).*
Silacci et al. (Proteomics 5:2340-2350 (2005)).*
Hoogenboom et al. (Nuc. Acids Res. 19(15):4133-4137 (1991)).*
de Haard et al. (JBC, 274(26):18218-18230 (1999)).*
De Jonge et al., "Production and Characterization of Bispecific Single-Chain Antibody Fragments," *Mol. Immunol.*, 32:1405-1412 (1995).
Hudson et al., "High avidity scFv multimers; diabodies and triabodies,"*J. Immunol. Methods*, 231:177-189 (1999).
Kipriyanov et al., "Effect of Domain Order on the Activity of Bacterially Produced Bispecific Single-chain Fv Antibodies," *J. Mol. Biol.*, 330:99-111 (2003).
Krebber et al., "Reliable cloning of functional antibody variable domains from hybridomas and spleen cell repertoires employing a reengineered phage display system," *J. Immunol. Methods*, 201:35-55 (1997).
Kurucz et al., "Retargeting of CTL by an Efficiently Refolded Bispecific Single-Chain Fv Dimer Produced in Bacteria," *J. Immunol.*, 154:4576-4582 (1995).
Little et al., "Of mice and men: hybridoma and recombinant antibodies," *Immunol. Today*, 21:364-370 (2000).
Peipp et al., "Bispecific antibodies targeting cancer cells," *Biochem. Soc. Trans.*, 30:507-511 (2002).
Plückthun et al., "New protein engineering approaches to multivalent and bispecific antibody fragments," *Immunotechnology*, 3:83-105 (1997).
Ridgway et al., "'Knobs-into-holes' engineering of antibody $C_H3$ domains for heavy chain heterodimerization," *Protein Eng.*, 9:617-621 (1996).
Shalaby et al., "Development of Humanized Bispecific Antibodies Reactive with Cytotoxic Lymphocytes and Tumor Cells Overexpressing the *HER2* Protooncogene," *J. Exp. Med.*, 175:217-225 (1992).

(Continued)

*Primary Examiner* — Lynn Bristol
(74) *Attorney, Agent, or Firm* — Fish & Richardson P.C.

(57) ABSTRACT

The present invention relates to methods of screening for commonly shared light chains, in which the method comprises the steps of (a) generating a host secreting the heavy chain of an antibody that binds to a desired antigen; (b) introducing an antibody light chain library into the host of step (a) to generate libraries presenting antibodies composed of the heavy chain and the light chains; (c) selecting a library presenting antibodies that bind specifically to the desired antigen of step (a); (d) introducing the library selected in step (c) into a host secreting the heavy chain of an antibody that binds to a desired antigen different from the antigen of step (a) to generate libraries that display antibodies composed of the heavy chains and light chains; and (e) selecting a library that displays antibodies that bind specifically to the desired antigen of step (d).

22 Claims, 2 Drawing Sheets

OTHER PUBLICATIONS

Skerra, "Use of the tetracycline promoter for the tightly regulated production of a murine antibody fragment in *Escherichia coli*," *Gene*, 151:131-135 (1994).

Völkel et al., "Optimized linker sequences for the expression of monomeric and dimeric bispecific single-chain diabodies," *Protein Eng.*, 14:815-823 (2001).

Zuo et al., "An efficient route to the production of an IgG-like bispecific antibody," *Protein Eng.*, 13:361-367 (2000).

Carter, "Bispecific human IgG by design," *J. Immunol. Methods*, 248:7-15 (2001).

Hoogenboom et al., "Multi-subunit proteins on the surface of filamentous phage: methodologies for displaying antibody (Fab) heavy and light chains," Nucleic Acids Res., 19:4133-7 (1991).

Merchant et al., "An efficient route to human bispecific IgG," Nat. Biotechnol., 16:677-81 (1998).

Cekaite et al., "Protein Arrays: A Versatile Toolbox for Target Identification and Monitoring of Patient Immune Responses," *Methods Mol. Biol.*, 360:335-348 (2007).

Andris-Widhopf et al., "Methods for the generation of chicken monoclonal antibody fragments by phage display", Journal of Immunological Methods, vol. 242, pp. 159-181, 2000.

DeNardo et al., "Anti-HLA-DR/anti-DOTA diabody construction in modular gene design platform: bispecific antibodies for pretargeted radioimmunotherapy", Cancer Biotherapy & Radiopharmaceuticals, vol. 16(6), pp. 525-535, 2001.

Holliger et al., "Diabodies", small bivalent and bispecific antibody fragments, Proc. Natl. Acad. Sci. USA, vol. 90, pp. 6444-6448, 1993.

McGuinness et al., "Phage diabody repertoires for selection of large No. Of bispecific antibody fragments", Nature Biotechnology, vol. 14(9), pp. 1149-1154, 1996.

Tang et al., "Selection of linkers for a catalytic single-chain antibody using phage display technology", The Journal of Biological Chemistry, vol. 271(26), pp. 15682-15686, 1996.

Turner et al., "Importance of the linker in expression of single-chain Fv antibody fragments: optimization of peptide sequence using phage display technology", Journal of Immunological Methods, vol. 205, pp. 43-54, 1997.

Casset et al., "A peptide mimetic of an anti-CD4 monoclonal antibody by rational design", Biochemical and Biophysical Research Communications 307:198-205, 2003.

Chen et al., "Selection and analysis of an optimized anti-VEGF antibody: crystal structure of an affinity-matured fab in complex with antigen", J. Mol. Biol. 293:865-881, 1999.

Holm et al., "Functional mapping and single chain construction of the anti-cytokeratin 8 monoclonal antibody TS1", Molecular Immunology 44:1075-1084, 2007.

Kumar et al., "Molecular cloning and expression of the fabs of human autoantibodies in *Escherichia coil* ", The Journal of Biological Chemistry 276(41):35129-35136, 2000.

MacCullum et al., "Antibody-antigen interactions: contact analysis and binding site topography", J. Mol. Biol. 262:732-745, 1996.

Pascalis et al., "Grafting of "abbreviated" complementarity-determining regions containing specificity-determining residues essential for ligand contact to engineer a less immunogenic humanized monoclonal antibody", The Journal of Immunology 169:3076-3084, 2002.

Smith-Gill et al., "Contributions of immunoglobulin heavy and light chains to antibody specificity for lysozyme and two haptens", The Journal of Immunology 139:4135-4144, 1997.

Song et al., "Light chain of natural antibody plays a dominant role in protein antigen binding", Biochemical and Biophysical Research Communications 268:390-394, 2000.

Vajdos et al., "Comprehensive functional maps of the antigen-binding site of an anti-ErbB2 antibody obtained with shotgun scanning mutagenesis", J. Mol. Biol. 320:415-428, 2002.

Wu et al., "Humanization of a murine monoclonal antibody by simultaneous optimization of framework and CDR residues", J. Mol. Biol. 294:151-162, 1999.

Griffiths et al., "Isolation of high affinity human antibodies directly from large synthetic repertoires," The EMBO Journal, 13(14):3245-3260 (1994).

* cited by examiner

METHODS OF SCREENING FOR ANTIBODY LIGHT CHAINS

CROSS-REFERENCE TO RELATED APPLICATIONS

This application is the National Stage of International Application No. PCT/JP2004/000496, filed Jan. 21, 2004, which claims the benefit of Japanese Patent Application No. 2003-012648, filed on Jan. 21, 2003. The contents of both applications are hereby incorporated by reference in their entireties.

TECHNICAL FIELD

The present invention relates to methods of screening for high-affinity light chains which correspond to, and are commonly shared by, heavy chains having different specificities for a multi-specific antibody.

BACKGROUND ART

Bispecific antibodies (BsAbs), also called bifunctional antibodies, are multivalent antibodies with specific binding sites for two antigenic determinants and which can react with two types of antigens. BsAbs can be produced using hybrid hybridomas, or more specifically, quadromas which are fusions of two different types of monoclonal antibody-producing cells (U.S. Pat. No. 4,474,893; R. Bos and W. Nieuwenhuitzen (1992) Hybridoma 11(1): 41-51). BsAbs can also be generated by linking Fab (antigen-binding) fragments or Fab' fragments of two types of monoclonal antibodies, using chemical techniques (M. Brennan et al. (1985) Science 229 (1708): 81-3) or by genetic engineering. In addition, BsAbs can be produced by covalently linking two complete monoclonal antibodies (B. Karpovsky et al. (1984) J. Exp. Med. 160(6): 1686-701).

Problems underlying BsAb production methods include the possibility of generating ten different types of antibody molecules due to random combination of immunoglobulin heavy chains and light chains (M. R. Suresh et al. (1986) Methods Enzymol. 121: 210-28). Among the ten types of antibodies produced by quadromas, the only antibody that has the desired dual specificity is the one that has the correct light and heavy chain combination and which is composed of two light chain/heavy chain pairs having different binding specificities. Therefore, the antibody having the desired dual specificity must be selectively purified from the ten types of antibodies produced by quadromas. Purification is generally performed using affinity chromatography, but this method is laborious and has low yields (Y. S. Massimo et al. (1997) J. Immunol. Methods 201: 57-66).

Methods that overcome such problems and give higher BsAb yields include, for example, methods of chemically linking antibody fragments such as Fab'-thionitrobenzoic acid derivative and Fab'-thiol (SH) (Brennan et al. (1985) Science 229: 81). Furthermore, methods for more conveniently obtaining chemically linkable Fab'-SH fragments include methods for producing these fragments from hosts such as E. coli using genetic recombination techniques (Shalaby et al. (1992) J. Exp. Med. 175: 217-25). Genetic recombination techniques can also be used to obtain BsAbs composed of humanized antibody fragments. Diabodies (Db) are BsAbs constructed from gene fusion of two types of fragments, and comprise a light chain variable region (VL) connected to a heavy chain variable region (VH) by a linker that is too short to allow pairing between them (P. Holliner et al. (1993) Proc. Natl. Acad. Sci. USA 90: 6444-8; EP No. 404,097; WO93/11161). An example of such a Db that has been further improved is single-chain Db (Japanese Patent Application No. 2002-112369). However, antibody fragments have a shorter serum half-life when compared to full-length antibodies, and do not have effector functions as complete antibodies do. Therefore, in some cases, full-length antibodies are more suitable for diagnosis and therapy.

Methods for efficiently linking generated antibody heavy chains into heterodimers include the method for introducing a sterically complementary mutation into the CH3 domain (a portion of the constant region) in the multimerized domain of an antibody heavy chain (Ridgway et al. (1996) Protein Eng. 9: 617-21). Heavy chains produced by this method may still form pairs with the wrong light chains. Patent Document 1 describes a method for generating multi-specific antibodies which share common light chains with heteromeric polypeptides having antigen-binding domains, and bind to these polypeptides.

BsAbs having specific binding capacities for two different antigens are useful as targeting agents in clinical fields such as in vitro and in vivo immunodiagnosis, therapy, and immunoassay. For example, they can be used as vehicles to link enzymes to carriers by designing a BsAb so that one of its arms binds to an epitope of an enzyme reaction non-inhibiting portion of an enzyme to be used in an enzyme immunoassay, and the other arm binds to a carrier for immobilization (Hammerling et al. (1968) J. Exp. Med. 128: 1461-73). Another example is antibody-targeted thrombolytic therapy. This therapy examines the use of antibodies that transport enzymes such as urokinase, streptokinase, tissue plasminogen activator, prourokinase, and such, and their precursor proteins, in a manner specific to fibrin in thrombi (T. Kurokawa et al. (1989) Bio/Technology 7: 1163; Unexamined Published Japanese Patent Application No. (JP-A) Hei5-304992). Furthermore, uses of BsAbs have been reported as potential mouse/human-chimeric bispecific antibodies for cancer targeting (JP-A Hei2-145187), and in cancer therapy and diagnosis for various tumors (see for example, JP-A Hei5-213775; JP-A Hei10-165184; JP-A Hei11-71288; Published Japanese Translation of International Publication No. 2002-518041; Published Japanese Translation of International Publication No. Hei11-506310; Link et al. (1993) Blood 81: 3343; T. Nitta et al. (1990) Lancet 335: 368-71; L. deLeij et al. (1990) Foundation Nationale de Transfusion Sanguine, Les Ulis France 249-53; Le Doussal et al. (1993) J. Nucl. Med. 34: 1662-71; Stickney et dl. (1991) Cancer Res. 51: 6650-5), mycotic therapy (JP-A Hei5-199894), immune response induction (Published Japanese Translation of International Publication Hei 10-511085; Weiner et al. (1993) Cancer Res. 53: 94-100), induotion of killer T-cell function (Kroesen et al. (1994) Br. J. Cancer 70: 652-61; Weiner et al. (1994) J. Immunol. 152: 2385), immunoanalysis (M. R. Suresh et al. (1986) Proc. Natl. Acad. Sci. USA 83: 7989-93; JP-A Hei5-184383), immunohistochemistry (C. Milstein and A. C. Cuello (1983) Nature 305: 537), and such.

Specific antibodies for a given antigen can be produced via genetic engineering, by obtaining the nucleotide sequences of heavy and light chain variable regions which determine the antigen specificity of antibodies (J. Xiang et al. (1990) Mol. Immunol. 27: 809; C. R. Bebbington et al. (1992) Bio/Technology 10:169). Methods for obtaining antigen-specific heavy chains and light chains include methods that utilize phages or phagemids using E. coli as the host (W. D. Huse et al. (1989) Science 246: 1275; J. McCafferty et al. (1990) Nature 348: 552; A. S. Kang et al. (1991) Proc. Natl. Acad. Sci. USA 88: 4363). In these methods, antibody libraries are constructed by generating Fabs, or by generating fusion proteins between a phage coat protein and Fab or single-strand Fv. Finally, antigenic affinity is examined to select antigen-specific antibodies and their genes from these antibody libraries.

[Patent Document 1] Published Japanese Translation of International Publication No. 2001-523971

BRIEF DESCRIPTION OF THE DRAWINGS

FIG. 1 is a schematic diagram of the Fab Lch library. DNA encoding an immunoglobulin heavy chain Fd fragment ("ANTI-AM Fd" that recognizes an epitope of interest (AR1) was cloned into a vector to generate the ANTI-AR1 Fd-expressing plasmid, p15LacIOP. This plasmid was expressed in a host cell, depicted as the large rectangle at the bottom of the figure. The host cell was infected with bacteriophage expressing a diverse immunoglobulin light chain library "Lch LIBRARY" in which the light chains are fused to a bacteriophage coat protein; the collection of plasmids that encode the light chain library is designated pELBG1ac1. Expression of the Fd and the light chains within the host cells results in the production of phage, each of which displays a recombinant antibody made up of the invariant Fd associated with one of the light chains ("Lch") of the library. One of these phage is illustrated in the upper right of the figure. It has ANTI-AR1Fd as the antibody heavy chain, with the CH1 region represented by a vertically striped oval and the VH region represented by a white oval. The antibody light chain is derived from the Lch library; it has a CL region represented by a cross-hatched oval and a VL region represented by a horizontally striped oval.

DISCLOSURE OF THE INVENTION

In generating a bispecific IgG two antibodies against different antigens are selected, and the two heavy chain genes and two light chain genes are introduced into cells, which gives rise to ten different combinations as mentioned in the Background Art. Patent Document 1 proposes developing a method for preferentially expressing a heteromeric combination of heavy chains by introducing an amino acid substitution at the CH3 portion of IgG, and efficiently expressing a bispecific IgG through the use of a commonly shared light chain. However, when two antibodies are randomly selected, the probability that they possess the same light chain is low, which makes it difficult to practice the above-mentioned idea. The present invention provides methods of screening for high-affinity light chains which correspond to arbitrary and different heavy chains, and which are commonly shared by the heavy chains.

Figure 1:
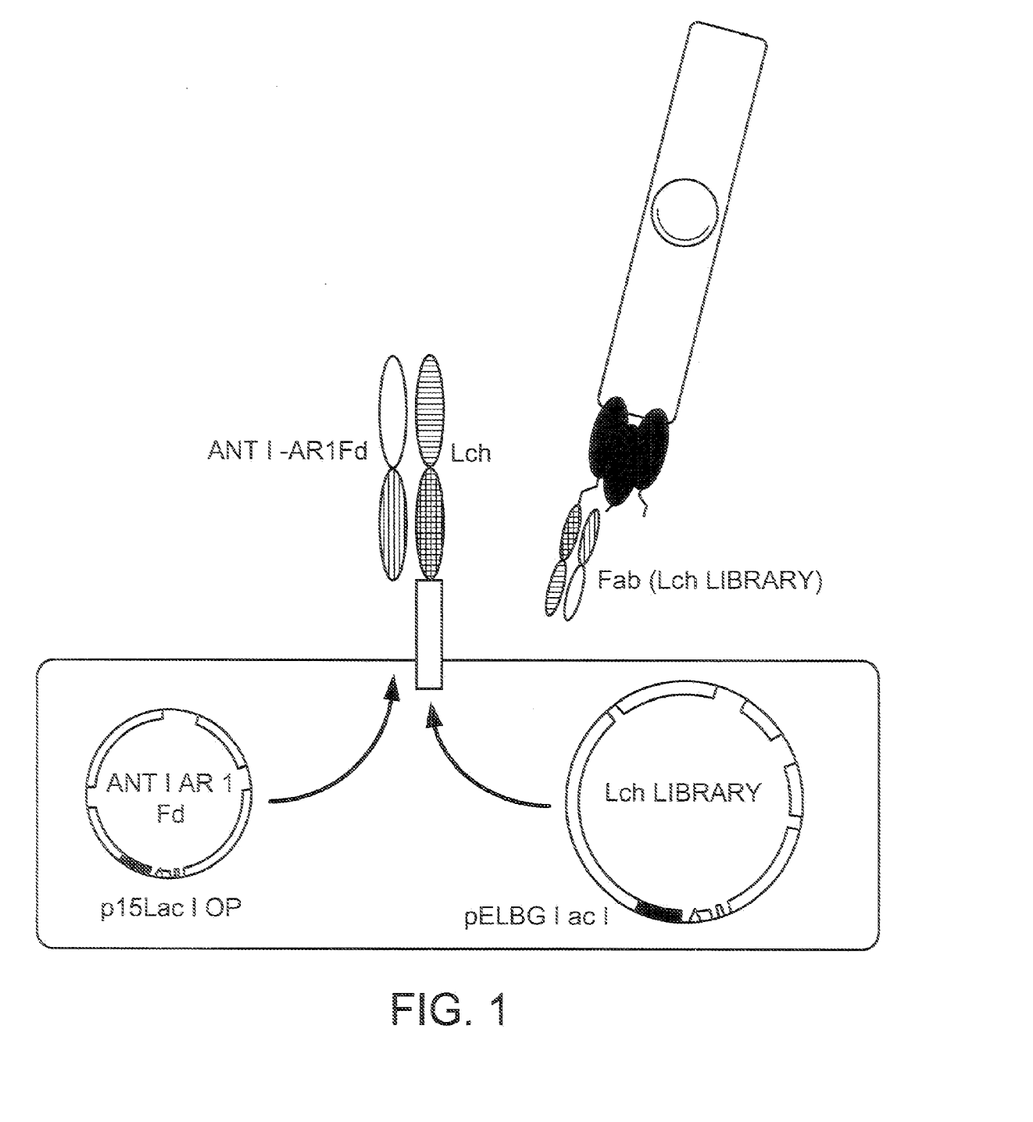
Figure 2:
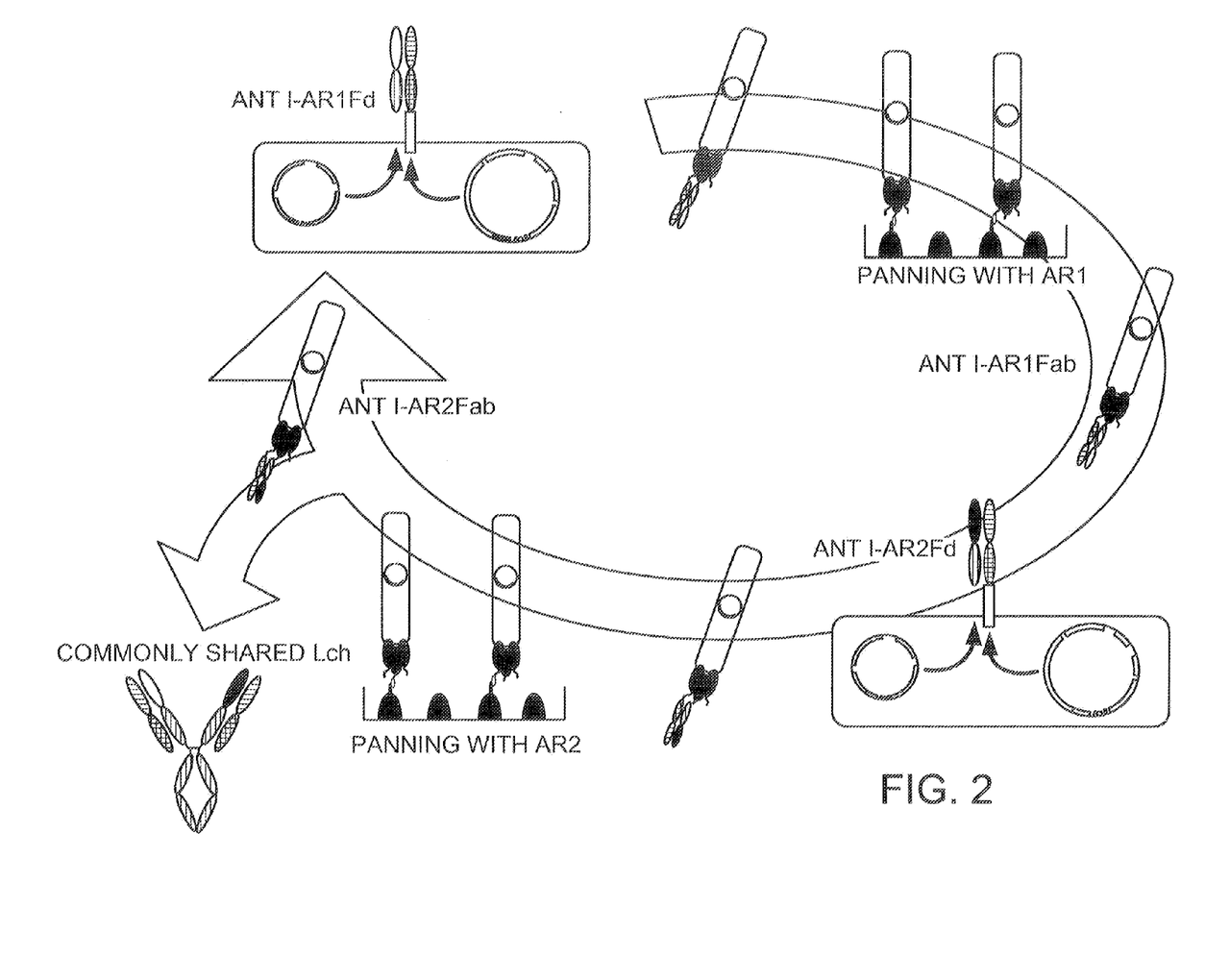
FIG. 2 is a schematic diagram showing a method of identifying an immunoglobulin light chain that can dimerize with each of two or more different immunoglobulin heavy chains and promote binding of each such heavy chain to its epitope. In this diagram, the process begins at the upper left, with the ANTI-AR1Fd/Lch library-expressing host cells that were depicted in FIG. 1. The antibody-displaying phage produced by those host cells are screened by panning with the antigen AR1, to select for light chains that increase the affinity of the ANTI-AR1Fd heavy chain for AR1. A new phage library encoding the selected light chains is used to infect a second host; the second host expresses an Fd fragment that recognizes an epitope that differs from AR1, e.g., AR2. This Fd fragment (ANTI-AR2Fd) is illustrated as vertically striped oval (representing the CH1 region) linked at its tip to a solid dark oval (representing the VH region). The antibody-displaying phage produced by this second type of phage-infected host cells are screened by panning with the AR2 antigen to select phage encoding light chains that increase the affinity of the ANTI-AR2Fd heavy chain for AR2. The resulting phage library ("ANTI-AR2Fab") encodes light chains, each of which can dimerize with either type of heavy chain and promote the binding of each type of heavy chain to its cognate antigen. The steps can be repeated for one or more additional rounds of selection (see up arrow). A selected light chain ("commonly shared light chain") capable of associating with both types of heavy chains can be used to create a bispecific antibody as depicted by the IgG shown in the lower left of the figure.

The present inventors completed this invention by discovering that, light chains with high antigenic affinity which correspond to, and are commonly shared by, different heavy chains that can be used to generate a BsAb, can be obtained by repeating the steps of: (1) individually selecting antibody A against antigen A and antibody B against antigen B; (2) introducing expression vectors carrying genes that encode the heavy chains (preferably the Fd portion, or more specifically, the region comprising VH and CH1) of the antibodies and preparing a secretory cell line for each heavy chain: Ha (which secretes the antibody A heavy chain) and Hb (which secretes the antibody B heavy chain); (3) separately constructing a library comprising light chains expressed as fusion proteins with phage surface proteins; (4) introducing the light chain library into the $E.\ coli$ Ha above, for secretion of a phage library that presents on their surfaces antibodies comprising the antibody A heavy chain and various light chains (Fab when the heavy chain is the Fd portion) (FIG. 1); (5) concentrating clones from the library by panning using antigen A; (6) infecting $E.\ coli$ Hb with the obtained clones, and obtaining a phage library that displays on their surfaces antibodies comprising the antibody B heavy chain and various light chains (Fab when the heavy chain is the Fd portion); and (7) concentrating library clones by panning with antigen B (FIG. 2).

More specifically, the present invention relates to the following:

(1) A method of screening for commonly shared light chains, wherein the method comprises the steps of:

(a) generating a host secreting the heavy chain of an antibody that binds to a desired antigen;

(b) introducing an antibody light chain library into the host of step (a) to cause secretion of phage libraries presenting antibodies composed of the heavy chain and the light chains;

(c) selecting a phage library that displays antibodies that bind specifically to the desired antigen of step (a);

(d) introducing the phage library selected in step (c) into a host secreting the heavy chain of an antibody that binds to a desired antigen different from the antigen of step (a) to cause secretion of phage libraries presenting antibodies composed of the heavy chains and light chains; and (e) selecting a phage library that displays antibodies that bind specifically to the desired antigen of step (d).

(2) A method of screening for commonly shared light chains, wherein the method comprises the steps of:

(a) generating a host-secreting the heavy chain of an antibody that binds to a desired antigen;

(b) introducing an antibody light chain library into the host of step (a) to cause secretion of phage libraries presenting antibodies composed of the heavy chain and the light chains;

(c) selecting a phage library that displays antibodies that bind specifically to the desired antigen of step (a);

(d) introducing the phage library selected in step (c) into a host secreting a heavy chain comprising an amino acid sequence different from that of the heavy chain of step (a) to cause secretion of phage libraries that display antibodies composed of the heavy chains and light chains; and (e) selecting a phage library that displays antibodies that bind specifically to the antigen recognized by the heavy chain of step (d).

3. The method of (1) or (2), wherein the antibody heavy chain is Fd and the antibody composed of said heavy chains and light chains is Fab.

4. The method of (1) or (2), wherein the host is *E. coli*.

5. The method of (1) or (2), wherein steps (b) to (e) are repeated twice or more.

6. The method of (1), wherein the method further comprises the following steps of:

(f) introducing the phage library selected in step (e) into a host secreting the heavy chain of an antibody that binds to a desired antigen different from the antigens of steps (a) and (d) to cause secretion of phage libraries that display antibodies composed of the heavy chains and light chains; and (g) selecting a phage library that displays antibodies that bind specifically to the desired antigen of step (f).

7. The method of (2), wherein the method further comprises the following steps of:

(f) introducing the phage library selected in step (e) into a host secreting a heavy chain comprising an amino acid sequence different from those of the heavy chains of steps (a) and (d) to cause secretion of phage libraries that display antibodies composed of the heavy chains and light chains; and (g) selecting a phage library that displays antibodies that bind specifically to the antigen recognized by the heavy chain of step (f).

8. A light chain obtained by the method of any one of (1) to (7).

9. An antibody comprising the light chain of (8).

10. A method for generating antibody light chains, wherein the method comprises the steps of:

(a) selecting an antibody light chain from the screening method of any one of claims 1 to 7;

(b) generating a vector capable of expressing the selected light chain based on its genetic sequence;

(c) introducing the vector into a host cell; and (d) culturing said host cell.

11. A host that is infected with a phage capable of presenting a light chain and comprises a vector capable of expressing a heavy chain.

12. An *E. coli* that is infected with a phage capable of presenting a light chain and comprises a vector capable of expressing a heavy chain.

The present invention relates to methods of screening for common light chains, in which the method comprises the steps of: (a) generating a host that secretes a heavy chain of an antibody which binds to a desired antigen; (b) introducing an antibody light chain library into the host of step (a) to generate libraries displaying antibodies composed of the heavy chain and the light chains above; (c) selecting a library which displays antibodies that bind specifically to the desired antigen described in step (a); (d) introducing the library selected in (c) into a host that secretes the heavy chain of an antibody which binds to a desired antigen different from the antigen of step (a) to generate a library that presents antibodies composed of the heavy chains and the light chains; and (e) selecting a library that presents antibodies which bind specifically to the desired antigen described in step (d). The methods of the present invention can be used to select commonly shared light chains that show high antigenic affinity and correspond to different heavy chains, particularly those that may be used to generate BsAbs. However, in the methods of the present invention, by repeating steps (b) and (c), or steps (b) to (e) using hosts that secrete different types of heavy chains and their corresponding antigens, one can screen for commonly shared light chains that correspond to a greater number of heavy chains and show high antigenic affinity, which can be used to produce not only BsAbs, but also multi-specific antibodies with specificity for three or more antigens. The multi-specific antibodies disclosed in this specification are antibodies that bind specifically to at least two types of different antigens. A preferred example of the multi-specific antibodies is a BsAb that can specifically bind to two antigens.

In the present invention, the term "different antigens" does not necessarily mean that the antigens themselves are different, and include cases where the antigenic determinants are different. Therefore, for example, different antigenic determinants within a single molecule are also included in the "different antigens" of the present invention. Two antibodies that each recognizes a different antigenic determinant within a single molecule are treated as antibodies recognizing different antigens in the present invention. Furthermore, the term "commonly shared light chain" in this invention refers to a light chain that associates with two or more different types of heavy chains, and may have a binding capacity for each of the antigens. Herein, "different heavy chains" refers to preferably heavy chains of antibodies against different antigens, but is not limited thereto, and also means heavy chains with amino acid sequences different from each other. Therefore, the present invention also relates to methods of screening for common light chains, wherein the method comprises the steps of (a) generating a host that secretes the heavy chain of an antibody which binds to a desired antigen, (b) introducing an antibody light chain library into the host of step (a) to generate libraries displaying antibodies composed of the heavy chain and light chains above, (c) selecting a library that presents antibodies which specifically bind to the desired antigen of step (a), (d) introducing the library selected in step (c) into a host which secretes a heavy chain having an amino acid sequence different from that of the heavy chain of step (a), and secreting a phage library that presents antibodies composed of the heavy chains and light chains, and (e) selecting a phage library that presents antibodies which specifically bind to the antigen recognized by the heavy chains of step (d).

The present invention relates to methods of screening for commonly shared light chains which correspond to two or more types of different antibody heavy chains and have high antigenic affinity. In the screening methods of the present invention, hosts which secrete heavy chains of antibodies that bind to desired antigens must be obtained first. Two types of hosts that each secretes a heavy chain corresponding to one of the two types of desired antigens are necessary for generating a BsAb, three types are necessary for a tri-specific antibody, and four types are necessary for a tetra-specific antibody. The following description will focus on examples of methods for screening commonly shared light chains in BsAbs.

To obtain hosts that secrete antibody heavy chains necessary for the screening of this invention, antibodies against two types of antigens. (called antigen A and antigen B for convenience) were selected, and cells producing them were obtained. In the description that follows, an antibody against antigen A is called antibody A, and an antibody against antigen B is called antibody B. These antibody-producing cells can be obtained by immunizing animals using appropriate sensitizing antigens. Alternatively, antibody-producing cells can be prepared by in vitro immunization of lymphocytes that can produce antibodies. Various mammals can be used as the immunizing animals, and primates and animals of Rodentia and Lagomorpha are generally used. Examples of such animals include mice, rats, and hamsters for Rodentia, rabbits for Lagomorpha, and monkeys including the cynomolgus monkey, rhesus monkey, hamadryas, and chimpanzees for primates. In addition, transgenic animals carrying human antibody gene repertoires are known, and human antibodies can be obtained by using such animals (see, WO96/34096; Mendez et al. (1997) Nat. Genet. 15: 146-56).

Animal immunization can be carried out by appropriately diluting and suspending a sensitizing antigen in Phosphate-Buffered Saline (PBS), physiological saline, or such, and forming an emulsion by mixing an adjuvant as necessary, followed by intraperitoneal or subcutaneous injection into animals. After that, the sensitizing antigen mixed with Freund's incomplete adjuvant is preferably administered several times every 4 to 21 days. Antibody production can be confirmed by measuring the target antibody titer in animal sera using conventional methods.

Both complete antibodies having immunogenicity and incomplete antigens (including haptens) having no immunogenicity may be used as antigens for immunizing animals. For example, substances comprising proteins, polypeptides, oligosaccharides, nucleic acids, lipids, or such may be used as antigens. Immunogens used to immunize animals can be made into soluble antigens by linking the molecules serving as antigens to other molecules (for example, keyhole limpet hemocyanin, serum albumin, bovine cycloglobulin, soybean trypsin inhibitor, and such) as necessary. Furthermore, in some cases, fragments of a soluble antigen can be used as immunogens. When transmembrane molecules such as receptors are used as an antigen, preferably a fragment thereof is used (for example, the extracellular region of a receptor). Furthermore, cells expressing transmembrane molecules on cell surfaces may be used as immunogens. Such cells can be found in nature (tumor cell lines and such), or prepared using genetic recombination techniques.

The methods of the present invention for selecting commonly shared light chains can be applied to the generation of BsAbs against various antigens. For example, when the objective is to use BsAbs for cancer therapy, one of the arms of the antibody is prepared so as to recognize tumor cell antigens, and the other arm can be designed to recognize a molecule that results in cytotoxicity. Examples of tumor cell antigens are 1D10 (malignant B cells), AMOC-1 (pan carcinoma associated antigen), CAMA1, CD7, CD15, CD19, CD22, CD38, CEA, EGF receptor, Id-1, 1-D1 (colon cancer), MoV18, p97, p185$^{HER2}$, OVCAR-3, neural cell adhesion molecule (NCAM), renal cell carcinoma, melanocyte stimulating hormone analog, and folic acid binding protein (FBP). Examples of molecules that result in cytotoxicity are CD3, CD16, and FcγRI. In addition, BsAbs can be designed so that they can bind IFN-α, saponin, vinca alkaloid, and toxins such as the A chain of ricin.

Furthermore, by constructing a BsAb in such a way that it binds to receptors (for example, various cytokine receptors) which upon ligand binding, transmit signals into cells by forming a heterodimer and changing the interchain distance, angle, and such, the BsAb can be utilized as an agonistic antibody to mimic receptor dimerization by ligands.

In addition, known BsAbs include (1) BsAbs which bind to CD30 and alkaline phosphatase to interact with enzymes that assist the conversion of chemical substances such as mitomycin phosphate into mitomycin alcohol, (2) BsAbs which bind to fibrin, tPA, uPA, and such and which can be used as fibrinolytic agents, (3) BsAbs which bind to LDL and Fc receptors (FcγRI, FcγRII, or FcγRIII), and such to guide immune complexes to cell surface receptors, (4) BsAbs which recognize antigens on T cells such as CD3, and antigens of pathogens such as HCV, influenza, and HIV, and which can be used for infectious diseases (5) BsAbs which have affinity towards tumor antigens that can be used to detect tumors, and towards detectable substances such as EOTUBE, DPTA, and hapten, (6) BsAbs which may be used as vaccine adjuvants (see, Fanger et al. (1992) Crit. Rev. Immunol. 12: 101-24), and (7) BsAbs against antigens which are detectable substances that may be used for diagnosis, such as rabbit IgG, horseradish peroxidase (HRP), FITC, and β-galactosidase, and hormone, ferritin, somatostatin, substance P, CEA, and such. The methods of the present invention for selecting commonly shared light chains can be used to generate various multi-specific antibodies including these known BsAbs (see WO89/02922 pamphlet, EP314, 317 publication, and U.S. Pat. No. 5,116, 964 publication).

Next, antibody-producing cells obtained from lymphocytes or animals immunized with a desired antigen can be fused with myeloma cells to generate hybridomas using conventional fusing agents, for example, polyethylene glycol (Goding (1986) Monoclonal Antibodies: Principles and Practice, Academic Press, 59-103). When needed, hybridoma cells are cultured and grown, and the binding specificity of the antibody produced from these hybridomas is analyzed using known methods such as immunoprecipitation, radioimmunoassay (RIA), and enzyme-linked immunosorbent assay (ELISA). Thereafter, hybridomas that produce antibodies of interest whose specificity, affinity, or activity has been determined can be subcloned by methods such as limiting dilution when needed.

Next, genes encoding the heavy chains of selected antibodies A and B are cloned from hybridomas or antibody-producing cells (sensitized lymphocytes, and such) using probes that may bind specifically to the heavy chains (for example, oligonucleotides complementary to sequences encoding the antibody constant regions). Cloning from mRNA using RT-PCR is also possible. Immunoglobulins are classified into five different classes, IgA, IgD, IgE, IgG, and IgM, which are further divided into several subclasses (isotypes) (for example, IgG-1, IgG-2, IgG-3, and IgG-4; IgA-1 and IgA-2; and such). The antibody heavy chains used in the present invention are not particularly limited and may belong to any of these classes or subclasses. However, IgG is particularly preferred.

Genes encoding antibodies or antibody fragments of interest can be obtained from antibody libraries rather than the hybridomas described above, by utilizing affinity for desired antigens. Construction of antibody libraries is well known, and they can be produced and used according to various methods. For example, for antibody phage libraries, one can refer to references such as Clackson et al. (1991) Nature 352: 624-8, Marks et al. (1991) J. Mol. Biol. 222: 581-97, Waterhouses et al. (1993) Nucleic Acids Res. 21: 2265-6, Griffiths et al. (1994) EMBO J. 13: 3245-60, Vaughan et al. (1996) Nature Biotechnology 14: 309-14, and Published Japanese Translation of International Publication No. Hei10-504970. In addition, known methods, such as methods which use eukaryotic cells as the library (WO95/15393 pamphlet), and the ribosome display method may be used.

Herein, it is possible to modify heavy chain-encoding genes by genetic engineering techniques. The technology of producing "humanized antibodies" by substituting portions of a monoclonal antibody derived from non-human mammals (mice, rats, hamsters, etc.) other than the CDR (complementarity determining region), with sequences of the framework structure of variable regions derived from human immunoglobulins by genetic engineering techniques is known (see for example, Jones et al. (1986) Nature 321: 522-5; Reichmann et al. (1988) Nature 332: 323-9; Presta (1992) Curr. Op. Struct. Biol. 2: 593-6). The humanized antibody may contain amino acid residues not included in the CDR or the framework structure sequences incorporated into the recipient antibody. Generally, such amino acid residues are introduced to optimize proper antigen recognition and/or binding capacity of antibodies. Heavy chains used in the screening methods of the present invention may be modified by humanization as such.

Besides the humanization described above, antibodies may be modified to improve their biological characteristics, for example, antigenic affinity. Such modifications can be made using methods such as site-directed mutagenesis (see for example, Kunkel (1985) Proc. Natl. Acad. Sci. USA 82: 488), PCR mutagenesis, and cassette mutagenesis. In general, mutant antibodies whose biological characteristics have been improved show amino acid sequence homology and/or similarity of 70% or higher, more preferably 80% or higher, and even more preferably 90% or higher (for example, 95% or higher, 97%, 98%, 99%, etc.), when compared to the amino acid sequence of the original antibody heavy chain variable region. In the present specification, sequence homology and/or similarity is defined as the ratio of amino acid residues that are homologous (same residue) or similar (amino acid residues classified into the same group based on the general characteristics of amino acid side chains) to the original antibody residues, after the sequence homology value has been maximized by aligning sequences and introducing gaps as necessary. Generally, naturally-occurring amino acid residues are classified into groups based on the characteristics of their side chains: (1) hydrophobic: alanine, isoleucine, norleucine, valine, methionine, and leucine; (2) neutral hydrophilic: asparagine, glutamine, cysteine, threonine, and serine; (3) acidic: aspartic acid, and glutamic acid; (4) basic: arginine, histidine, and lysine; (5) residues that affect the orientation of the chains: glycine, and proline; and (6) aromatic: tyrosine, tryptophan, and phenylalanine.

Host cells that secrete antibody heavy chains used in the methods of the present invention may be those that secrete full-length antibody heavy chains, or those that secrete partial fragments of the heavy chains. Therefore, the heavy chains of the present invention comprise full-length antibody heavy chains and heavy chain fragments. The heavy chain fragments are not particularly limited, and preferably comprise a heavy chain variable region. It is particularly preferred that they comprise an Fd portion (heavy chain variable region VH and constant region CH1). However, without particular limitation to those described above, the host cells may be constructed to secrete only the heavy chain variable region, a portion of the variable region, or a portion containing other regions of the constant region (CH2 and 3).

A gene portion that encodes a desired antibody heavy chain is introduced into an expression vector that is suitable for expression in appropriate host cells. In the methods of the present invention, host cells that secrete heavy chains are not particularly limited, and are preferably bacteria that can be infected by phages, particularly gram negative bacteria. Among them, E. coli that express the F-factor are preferred. An example of E. coli that express the F-factor is XL1-Blue.

In the methods of the present invention, particularly preferred vectors for expressing heavy chains in E. coli must comprise units such as promoters and terminators, which regulate the transcription and translation of genetic information. For example, pBR and pUC-type plasmids can be used as the plasmid vector. Promoters such as lac, trp, tac, and those derived from λ phage PL and PR may be utilized as the promoter. Terminators derived from trpA, phages, and rrnB ribosomal RNA can be used as the terminator.

The constructed expression vectors are introduced into host cells, and strains that secrete antibody heavy chains are obtained. The expression vectors may be introduced into host cells using methods such as those that utilize calcium ions (Proc. Natl. Acad. Sci. USA 69: 2110 (1972)), protoplast methods (JP-A Sho 63-24829), and electroporation methods (Gene 17: 107 (1982); Molecular & General Genetics 168: 111 (1979)).

In the screening methods of the present invention, the subject of screening, a pool of antibody light chains, is preferably in the form of a phage library when bacterial cells are selected as the host cell for secretion of heavy chains. For light chain-encoding genes, populations of genes obtained by amplifying RNA derived from substances prepared from peripheral blood monocytes, bone marrow, or spleen of humans or other animals, using methods such as reverse transcription polymerase chain reaction (RT-PCR), synthesized DNA, and such, may be used. In addition, methods for increasing the diversity of an antibody library by inducing mutations in the antibody CDR region are also known (Published Japanese Translation of International Publication No. Hei 10-504970). A library of antibody light chain genes with its diversity increased by such methods can be used as a pool of light chain-encoding genes in the screening methods of the present invention. The light chains of the present invention comprise full-length light chains and partial fragments of light chains. The light chain fragments are not particularly limited, and are preferably fragments comprising the light chain variable region VL.

Generally, to generate a phage library, light chain-encoding DNAs are incorporated into appropriate phage vectors, so that the light chains will be displayed on the external surface of the phages, as fusion proteins with coat proteins or display anchor proteins. Herein, there are no particular limitations on the phage vectors. Generally, they are vectors that contain a bacteriophage replication origin (ori), and are induced through modifications of the phage genome. Phage vectors preferably encode, in the direction from N to C terminus, (1) a light chain, and (2) a phage membrane anchor domain (all or a portion of a coat protein or display anchor protein). Furthermore, a sequence encoding the prokaryotic cell secretion signal domain, which enables proteins encoded by the abovementioned (1) and (2) to be secreted to the outside of host bacterial cells and incorporated into bacteriophages, is placed before the sequence encoding the light chain of (1), as necessary.

A phage membrane anchor domain for displaying light chains on the surface of phage particles is an entire coat protein or display anchor protein, or a portion thereof, which can bind to the outer membrane of a filamentous phage particle and therefore allow fusion proteins to be incorporated. Coat proteins or display anchor proteins are proteins that coat mature phage particles, and can be exemplified by the major phage particle coat protein cpVIII, minor coat proteins such as cpVI, cpVII, and cpIX, and infection-related adsorption protein cpIII. Expression as a fusion protein with the cpIII or cpVIII protein is particularly preferred, and of these, the expression of the fusion proteins formed with cpIII is well studied (see, Smith (1985) Science 228: 1315-7; de la Cruz et al. (1988) J. Biol. Chem. 263: 4318-22). The membrane anchor domain comprises a portion of the C-terminal region of a protein coating these mature phage particles, in other words, are a region of hydrophobic amino acid residues for penetrating lipid bilayer membranes, and a region of charged amino acid residues in the cytoplasmic region.

Secretion signals can be any leader peptide sequence that enables secretion of fusion proteins from host cells; one such example being the pel1B secretion signal (see, Better et al. (1988) Science 240: 1041-3; Sastry et al. (1989) Proc. Natl. Acad. Sci. USA 86: 5728).

Generally, phage genome sequences necessary for the production of phage particles are removed or inactivated in the phage vectors mentioned above. Therefore, to produce phage particles via infection of host cells with the phage vectors, helper phages are generally required. Helper phages are used to infect cells comprising defective phages or phage vectors, and have a function of complementing defective phages or phage vectors.

There are no particular limitations on the phage particles that constitute the phage libraries, and for example, known phages such as Charon4A, Charon30, f1, f2, fd, G4, If1, Ike, M13, MS2, P1, P2, P4, Pf1, Pf3, T4, T7, Xf, λ, λB, λgWES, ΦK, and ΦX174, may be utilized, and filamentous phages such as fd, f1, and M13 are preferred. Every library phage particle produced in this manner comprises a copy of its corresponding phagemid, which encodes the light chain fusion protein presented on the particle surface. Therefore, genes encoding light chains that associate with the antibody A heavy chain and have binding capacity for antigen A can be obtained, by contacting the antibody A heavy chain with a light chain-presenting phage library, and separating phage particles based on their antigen A-binding capacity, where the heavy chain is bound to the light chain fusion protein presented on the phage particle.

For example, a vector comprising the f1 phage ori is used to construct a library in which light chains (for example, those comprising VL and CL) are expressed as fusion proteins with the f1 phage gene 3 protein (minor coat protein). This light chain library is introduced into the aforementioned E. coli host which expresses an antibody A heavy chain (for example, Fd), and by infecting the host with helper phages, a phage library, which presents on their surfaces antibodies comprising an antibody A heavy chain and various light chains (Fab when the heavy chain is Fd and the light chain comprises VL and CL) as fusion proteins with the gene 3 protein, can be secreted from E. coli (FIG. 1).

WO95/15393 also proposes construction of antibody libraries using eukaryotic cells, which allows more accurate investigation of the actual antigen-binding capacity of antibodies from the screening stage. Therefore, in place of bacterial hosts such as E. coli, the methods of the present invention can also employ antibody libraries from eukaryotic cells that present antibodies on their cell surfaces. More specifically, an expression vector carrying a gene that encodes a desired heavy chain (for example, Fd), and is linked downstream of a promoter appropriate for its expression and a signal sequence which enables the secretion of the heavy chain, is introduced into eukaryotic host cells. Furthermore, expression vectors are constructed with light chain-encoding genes linked to a transmembrane region-encoding sequence and inserted downstream of an appropriate promoter, so that the light chains will be displayed on cell surfaces when expressed. The transmembrane region is preferably added to the C terminus of expressed light chains. By introducing light chain expression vectors into the aforementioned heavy chain-secreting host cells, host cells which express on their cell surfaces antibodies that bind to a desired antigen can be selected. The displayed antibody is a Fab fragment when Fd is used as the heavy chain and those comprising VL and CL are used as the light chains.

There are no particular limitations as to the type of host cell used, but when the objective is to screen antibodies with accurate antigen specificity, the use of eukaryotic cells, particularly animal cells, is preferred. Even more preferable are mammalian cells. Examples include 3T3, BHK, Bowes melanoma, C127, CHO (J. Exp. Med. 108: 945 (1995); Proc. Natl. Acad. Sci. 77: 4216 (1980); Proc. Natl. Acad. Sci. USA (1968)), COS, HEK, Hela, KJM, Namalwa, and myeloma cells. Vectors for expressing heavy chains and light chains can be any vector suitable for expression in the host of choice, which can be constructed using pUC18 and such. A heavy chain-encoding gene can be incorporated into a genome using well-known techniques. Expression vectors are introduced into host cells by conventional methods such as electroporation (Chu et al. (1987) Nucleic Acids Res. 15: 1311-26), the cationic liposome method, direct injection (microinjection), electroporation (Current Protocols in Molecular Biology, John Wiley&Sons (1987) Section 9.1-9.9), lipofection ((Derijard (1994) Cell 7: 11025-37), the calcium phosphate method (Chen and Okayama (1987) Mol. Cell. Biol. 7: 2745-52), and the DEAE dextran method (Lopata et al. (1984) Nucleic Acids Res. 12: 5707-17; Sussmann and Milman (1985) Mol. Cell. Biol. 4: 1642-3).

Next, in the screening methods of the present invention, host cells that present antibodies produced as described above are selected based on their affinity for antigen A. When bacterial cells are selected as the host and light chain-encoding genes as the phage library, antibodies are secreted from host cells as phage libraries. Therefore, panning with antigen A directed against antibody A enables concentration of clones that bind to antigen A from the host cell-secreted phage library. In this case, the concentrated phage library of interest can be directly used in the subsequent step of infecting host cells, and is therefore particularly convenient. When the phage library is not secreted, but is in the form of antibodies presented on the host cell surface, expression vectors harboring light chains that constitute the desired antibodies are collected from cells presenting these antibodies, and purified by known techniques as necessary and used in the following step.

Next in the screening methods of the present invention, the clones concentrated as above, or light chain expression vectors that have been recovered, are introduced or used to infect host cells that secrete the antibody (for example, Fd) of antibody B. When using a phage library, by heavily infecting these host cells with helper phages, a phage library that presents on its surface antibodies comprising an antibody B heavy chain such as Fd and various light chains, is secreted (Fab when Fd and light chains comprising VL and CL are used). When expression vectors other than phage vectors are used, various cells which present on their surfaces antibodies comprising a heavy chain (for example, Fd) and antibody B light chains are obtained (Fab when Fd and light chains comprising VL and CL are used).

Next, similarly to the selection against antigen A, when a phage library is used, clones that bind to antigen B are concentrated from the host cell-secreted phage library by panning with antigen B. When the phage library is in the form of antibodies presented on host cell surfaces, expression vectors harboring light chains that constitute the desired antibodies are collected from cells that present these antibodies, and purified by known techniques as necessary. By screening light chains against antigen A and antigen B as described above, commonly shared light chains that correspond to different heavy chains and show high affinity towards various antigens can be screened (FIG. 2).

Furthermore, commonly shared light chains with high selectivity can be screened by repeating infection/introduction into hosts that secrete antibodies (such as Fd) against antigen A and antigen B, secretion/presentation of antibodies (or antibody fragments corresponding to the light chains and heavy chains used, such as Fab), and panning/selection as necessary. Furthermore, by expanding the types of antigens to be screened, commonly shared light chains that correspond to a larger number of heavy chains and show high affinity towards various antigens can be screened. Light chains selected in this manner and genes encoding the light chains can be utilized for the production of multi-specific antibodies including BsAbs, which are useful in various diagnostic and therapeutic methods.

INDUSTRIAL APPLICABILITY

The methods of the present invention enable screening of commonly shared light chains that correspond to different heavy chains and show high affinity. Multi-specific antibodies can be efficiently expressed by utilizing the method of this invention.

The invention claimed is:

1. A screening method comprising:
    (a) providing a first plurality of bacterial host cells secreting a first Fd of a single antibody species that binds to a first antigen;
    (b) introducing an antibody light chain phage library encoding a plurality of different light chains, each linked to a bacterial secretion signal and a phage membrane anchor domain, into the first plurality of host cells to cause secretion of phage libraries presenting two-chain antibody fragments, each antibody fragment comprising the first Fd and a light chain;
    (c) selecting a phage library that displays antibody fragments that bind specifically to the first antigen;
    (d) introducing the phage library selected in step (c) into a second plurality of bacterial host cells secreting a second Fd that is different from the first Fd and is the Fd of a single antibody species that binds to a second antigen different from the first antigen, to create phage libraries presenting two-chain antibody fragments, each comprising the second Fd and a light chain; and
    (e) selecting, from the phage libraries created in step (d), a phage library that displays two-chain antibody fragments that bind specifically to the second antigen.

2. The method of claim 1, wherein the host is *E. coli*.

3. The method of claim 1, wherein steps (b) to (e) are carried out twice or more, with each subsequent round beginning with the phage library selected in step (e) of the prior round.

4. The method of claim 1, wherein the method further comprises the steps of:
    (f) introducing the phage library selected in step (e) into a third plurality of bacterial host cells secreting a third Fd that is different from the first and second Fd's and is the Fd of a single antibody species that binds to a third antigen different from the first and second antigens, to create phage libraries that display two-chain antibody fragments comprising the third Fd and a light chain; and
    (g) selecting a phage library that displays two-chain antibody fragments that bind specifically to the third antigen.

5. The method of claim 2, wherein the bacterial secretion signal is pel1B.

6. A method for generating antibody light chains, wherein the method comprises the steps of:
    (i) carrying out the method of claim 1;
    (ii) selecting, from the phage library selected in (e), a phage encoding an antibody light chain (the "selected light chain");
    (iii) generating a vector capable of expressing the selected light chain based on its genetic sequence;
    (iv) introducing the vector into a host cell; and
    (v) culturing said host cell of (iv).

7. A method of producing a multi-specific antibody, the method comprising
    (i) carrying out the screening method of claim 1 to select a phage library that displays two-chain antibody fragments that bind specifically to the second antigen;
    (ii) selecting from the phage library of (i) a phage displaying a two-chain antibody fragment that binds to the second antigen and comprises the second Fd and a light chain (the "selected light chain");
    (iii) producing a host cell comprising nucleic acid encoding (A) the selected light chain, (B) a heavy chain comprising the sequence of the first Fd, and (C) a heavy chain comprising the sequence of the second Fd;
    (iv) culturing the host cell of (iii) so that it expresses (A), (B), and (C) and assembles (A), (B) and (C) into a multispecific antibody comprising a copy of (B), a copy of (C), and two copies of (A), wherein (A) serves as a common light chain for both (B) and (C).

8. The method of claim 7, wherein the host is *E. coli*.

9. The method of claim 8, wherein the bacterial secretion signal is pel1B.

10. A method of producing a multi-specific antibody, the method comprising
    (i) carrying out the screening method of claim 3 to ultimately select a phage library that displays two-chain antibody fragments that bind specifically to the second antigen;
    (ii) selecting from the phage library of (i) a phage displaying a two-chain antibody fragment that binds to the second antigen and comprises the second Fd and a light chain (the "selected light chain");
    (iii) producing a host cell comprising nucleic acid encoding (A) the selected light chain, (B) a heavy chain comprising the sequence of the first Fd, and (C) a heavy chain comprising the sequence of the second Fd;
    (iv) culturing the host cell of (iii) so that it expresses (A), (B), and (C) and assembles (A), (B) and (C) into a multispecific antibody comprising a copy of (B), a copy of (C), and two copies of (A), wherein (A) serves as a common light chain for both (B) and (C).

11. The method of claim 10, wherein the host is *E. coli* and the bacterial secretion signal is pel1B.

12. A screening method comprising:
    (a) providing a first plurality of bacterial host cells secreting a first Fd of a single antibody species that binds to a first antigen;
    (b) introducing an antibody light chain phage library encoding a plurality of different light chains, each linked to a bacterial secretion signal and a phage membrane anchor domain, into the first plurality of host cells to cause secretion of phage libraries presenting two-chain antibody fragments, each antibody fragment comprising the first Fd and a light chain;
    (c) selecting a phage library that displays antibody fragments that bind specifically to the first antigen;
    (d) introducing the phage library selected in step (c) into a second plurality of bacterial host cells secreting a second Fd comprising an amino acid sequence different from that of the first Fd, wherein the second Fd is the Fd of a single antibody species, to create phage libraries displaying two-chain antibody fragments, each antibody fragment comprising the second Fd and a light chain; and (e) selecting, from the phage libraries created in step (d), a phage library that displays antibody fragments that bind specifically to an antigen recognized by the second Fd.

13. The method of claim 12, wherein the method further comprises the steps of:
   (f) introducing the phage library selected in step (e) into a third plurality of bacterial host cells secreting a third Fd comprising an amino acid sequence different from those of the first and second Fd's, wherein the third Fd is the Fd of a single antibody species, to cause secretion of phage libraries that display two-chain antibody fragments, each being composed of the third Fd and a light chain; and
   (g) selecting a phage library that displays antibody fragments that bind specifically to an antigen recognized by the third Fd.

14. The method of claim 12, wherein the host is *E. coli*.

15. The method of claim 12, wherein steps (b) to (e) are carried out twice or more, with each subsequent round beginning with the phage library selected in step (e) of the prior round.

16. The method of claim 14, wherein the bacterial secretion signal is pel1B.

17. A method for generating antibody light chains, wherein the method comprises the steps of:
   (i) carrying out the method of claim 12;
   (ii) selecting, from the phage library selected in (e), a phage encoding an antibody light chain the "selected light chain");
   (iii) generating a vector capable of expressing the selected light chain based on its genetic sequence;
   (iv) introducing the vector into a host cell; and
   (v) culturing said host cell of (iv).

18. A method of producing a multi-specific antibody, the method comprising
   (i) carrying out the screening method of claim 12 to select a phage library that displays two-chain antibody fragments that bind specifically to the antigen recognized by the second Fd;
   (ii) selecting from the phage library of (i) a phage displaying a two-chain antibody fragment that binds to the antigen recognized by the second Fd and comprises the second Fd and a light chain (the "selected light chain");
   (iii) producing a host cell comprising nucleic acid encoding (A) the selected light chain, (B) a heavy chain comprising the sequence of the first Fd, and (C) a heavy chain comprising the sequence of the second Fd;
   (iv) culturing the host cell of (iii) so that it expresses (A), (B), and (C) and assembles (A), (B) and (C) into a multispecific antibody comprising a copy of (B), a copy of (C), and two copies of (A), wherein (A) serves as a common light chain for both (B) and (C).

19. The method of claim 18, wherein the host is *E. coli*.

20. The method of claim 19, wherein the bacterial secretion signal is pel1B.

21. A method of producing a multi-specific antibody, the method comprising
   (i) carrying out the screening method of claim 13 to ultimately select a phage library that displays two-chain antibody fragments that bind specifically to the antigen recognized by the third Fd;
   (ii) selecting from the phage library of (i) a phage displaying a two-chain antibody fragment that binds to the antigen recognized by the third Fd and comprises the third Fd and a light chain (the "selected light chain");
   (iii) producing a host cell comprising nucleic acid encoding (A) the selected light chain, (B) a heavy chain comprising the sequence of the first Fd, (C) a heavy chain comprising the sequence of the second Fd, and (D) a heavy chain comprising the sequence of the third Fd;
   (iv) culturing the host cell of (iii) so that it expresses (A), (B), (C), and (D) and assembles (A), (B), (C), and (D) into a multispecific antibody comprising a copy of (B), a copy of (C), a copy of (D), and three copies of (A), wherein (A) serves as a common light chain for all of (B), (C), and (D).

22. The method of claim 21, wherein the host is *E. coli* and the bacterial secretion signal is pel1B.

* * * * *